United States Patent [19]

Wirth et al.

[11] 4,290,940
[45] Sep. 22, 1981

[54] PYRROLE STABILIZERS FOR CHLORINE-CONTAINING THERMOPLASTICS

[75] Inventors: Hermann O. Wirth; Jürgen Büssing, both of Bensheim; Hans-Helmut Friedrich, Lautertal, all of Fed. Rep. of Germany

[73] Assignee: Ciba-Geigy Corporation, Ardsley, N.Y.

[21] Appl. No.: 164,194

[22] Filed: Jun. 30, 1980

[30] Foreign Application Priority Data

Jun. 28, 1979 [CH] Switzerland .................. 6035/79

[51] Int. Cl.³ .............. C07D 207/32; C07D 207/333; C08K 5/34
[52] U.S. Cl. .................. 260/45.8 N; 260/23 XA; 260/45.7 PH; 260/45.75 Q; 260/45.75 W; 260/313.1
[58] Field of Search .................. 260/45.8 N

[56] References Cited

U.S. PATENT DOCUMENTS

| | | | |
|---|---|---|---|
| 2,208,216 | 7/1940 | Johnson et al. | 260/45.8 N |
| 2,302,362 | 11/1942 | Nelles et al. | 260/45.8 N |
| 2,780,626 | 2/1957 | Brown et al. | 260/45.8 N |
| 2,946,765 | 7/1960 | Roos et al. | 260/45.8 NH |
| 2,993,021 | 7/1961 | Bavley et al. | 260/45.8 N |
| 3,225,061 | 12/1965 | Braus et al. | 260/45.8 N |
| 3,478,053 | 11/1969 | Szmuszkovicz | 260/45.8 N |
| 3,644,631 | 2/1972 | Pachter et al. | 424/274 |
| 4,093,586 | 6/1978 | Stephen | 260/45.8 N |
| 4,111,901 | 9/1978 | Hechenbleikner | 260/45.8 N |
| 4,209,440 | 6/1980 | Pigerol et al. | 260/45.8 N |

*Primary Examiner*—Harold D. Anderson
*Assistant Examiner*—R. A. White
*Attorney, Agent, or Firm*—Harry Falber

[57] ABSTRACT

Chlorine-containing thermoplastics, containing a pyrrole of the formula I

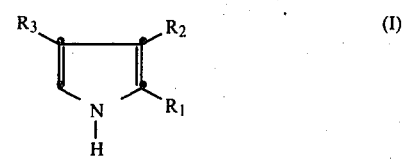

in which $R_1$ is hydrogen, alkyl, cycloalkyl, aryl, alkoxycarbonylmethyl, free or esterified α-hydroxyalkyl, free or esterified α-hydroxycycloalkylmethyl, free or esterified α-hydroxyaralkyl, alkoxymethyl, alkylthiomethyl, aryloxymethyl, arylthiomethyl, cycloalkoxymethyl, cycloalkylthiomethyl, aralkoxymethyl, aralkylthiomethyl, alkoxy, alkylthio, cycloalkoxy, cycloalkylthio, aralkoxy, arylalkylthio, aryloxy, arylthio, halogen, mercapto, mercaptomethyl or hydroxyl, $R_2$ is hydrogen, alkyl, cycloalkyl, aryl, free or esterified α-hydroxyalkyl, in which the alkyl moiety together with $R_1$ can be alkylene, or free or esterified α-hydroxycycloalkylmethyl, free or esterified α-hydroxyaralkyl, alkoxy, cycloalkoxy, aralkoxy, aryloxy, alkylthio, cycloalkylthio, aralkylthio, arylthio, alkoxymethyl, alkylthiomethyl, aryloxymethyl, arylthiomethyl, cycloalkoxymethyl, cycloalkylthiomethyl, aralkoxymethyl, aralkylthiomethyl, hydroxyl, cyano, free carboxyl or carboxyl in the form of a salt or an ester, or acyl, it being possible for acyl together with $R_1$ to be —CO-alkylene, in which —CO— is bonded in the 3-position, or $R_2$ is halogen, mercapto or mercaptomethyl, and $R_3$ is alkyl, cycloalkyl, aralkyl, aryl, free or esterified hydroxymethyl, alkoxymethyl, alkylthiomethyl, cycloalkoxymethyl, cycloalkylthiomethyl, aralkoxymethyl, aralkylthiomethyl, aryloxymethyl or arylthiomethyl, alkoxy, alkylthio, cycloalkoxy, cycloalkylthio, aralkoxy, aralkylthio, aryloxy, arylthio, halogen, mercapto or mercaptomethyl, or if $R_2$ is carboxyl in the form of a salt, $R_3$ is hydrogen and $R_1$ is as defined, or in which $R_3$ is hydroxyl and $R_1$ is hydrogen, alkyl or aryl and $R_2$ is hydrogen, alkyl, aryl or acyl, or a salt thereof.

13 Claims, No Drawings

PYRROLE STABILIZERS FOR CHLORINE-CONTAINING THERMOPLASTICS

The present invention relates to the stabilisation of chlorine-containing thermoplastics by the addition of pyrroles, and also to novel pyrroles.

It is known that chlorine-containing polymers must be protected against the harmful influence of light and heat, for example when processing to mouldings. Hitherto, in particular organo-tin compounds, metal carboxylates or aminocrotonates have been used for this purpose. However, the stabilities achieved with these active compounds are not always adequate for practical purposes and there is a need to find improvements here and in particular to provide better metal-free heat stabilisers for PVC. One stabiliser for PVC which has been known for a long time is 2-phenylindole, cf. Voigt "Stabilisierung der Kunststoffe" ("Stabilisation of Plastics"), Springer-Verlag, 1966, page 306, but this gives satisfactory results only in combination with metal carboxylates.

U.S. Pat. Nos. 3,404,159, 3,573,216 and 3,404,161 disclose pyrrole-malonitriles which are suitable as UV absorbers and light stabilisers, inter alia also for PVC, because of their specific absorption between 250 and 400 m$\mu$. U.S. Pat. No. 3,478,053 discloses 2,3-diarylpyrroles for the same purpose. These patent specifications were not able to contribute to the development of improved heat stabilisers, which was the object of the present invention.

The invention relates to chlorine-containing thermoplastics, containing a pyrrole of the formula I

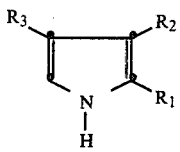

in which $R_1$ is hydrogen, alkyl, cycloalkyl, aryl, alkoxycarbonylmethyl, free or esterified $\alpha$-hydroxyalkyl, free or esterified $\alpha$-hydroxycycloalkylmethyl, free or esterified $\alpha$-hydroxyaralkyl, alkoxymethyl, alkylthiomethyl, aryloxymethyl, arylthiomethyl, cycloalkoxymethyl, cycloalkylthiomethyl, aralkoxymethyl, aralkylthiomethyl, alkoxy, alkylthio, cycloalkoxy, cycloalkylthio, aralkoxy, arylalkylthio, aryloxy, arylthio, halogen, mercapto, mercaptomethyl or hydroxyl, $R_2$ is hydrogen, alkyl, cycloalkyl, aryl, free or esterified $\alpha$-hydroxyalkyl, in which the alkyl moiety together with $R_1$ can be alkylene, or free or esterified $\alpha$-hydroxycycloalkylmethyl, free or esterified $\alpha$-hydroxyaralkyl, alkoxy, cycloalkoxy, aralkoxy, aryloxy, alkylthio, cycloalkylthio, aralkylthio, arylthio, alkoxymethyl, alkylthiomethyl, aryloxymethyl, arylthiomethyl, cycloalkoxymethyl, cycloalkylthiomethyl, aralkoxymethyl, aralkylthiomethyl, hydroxyl, cyano, free carboxyl or carboxyl in the form of a salt or an ester, or acyl, it being possible for acyl together with $R_1$ to be —CO-alkylene, in which —CO— is bonded in the 3-position, or $R_2$ is halogen, mercapto or mercaptomethyl, and $R_3$ is alkyl, cycloalkyl, aralkyl, aryl, free or esterified hydroxymethyl, alkoxymethyl, alkylthiomethyl, cycloalkoxymethyl, cycloalkylthiomethyl, aralkoxymethyl, aralkylthiomethyl, aryloxymethyl or arylthiomethyl, alkoxy, alkylthio, cycloalkoxy, cycloalkylthio, aralkoxy, aralkylthio, aryloxy, arylthio, halogen, mercapto or mercaptomethyl, or if $R_2$ is carboxyl in the form of a salt, $R_3$ is hydrogen, and $R_1$ is as defined, or in which $R_3$ is hydroxyl and $R_1$ is hydrogen, alkyl or aryl and $R_2$ is hydrogen, alkyl, aryl or acyl, or a salt thereof.

It has been found, surprisingly, that the pyrroles used according to the invention are outstandingly effective stabilisers, in particular for PVC, which do not have the disadvantages of the prior art or do not have the disadvantages to the same degree, and in particular do not necessarily have to be combined with metal compounds.

Alkyl $R_1$ has, in particular, 1–6 C atoms, such as ethyl, n-propyl or in particular methyl. Cycloalkyl $R_1$ has, in particular 5–8 C atoms and is, in particular, cyclohexyl or cyclopentyl. Aryl $R_1$ is phenyl, which can be substituted, for example by $C_{1-6}$ alkyl, such as methyl, $C_{1-6}$ alkoxy, such as methoxy, and/or hydroxyl, and is, for example, m-hydroxyphenyl and in particular phenyl itself. Alkoxycarbonylmethyl $R_1$ has, in particular, 1–18 C atoms in the alkoxy moiety, such as methoxycarbonylmethyl or ethoxycarbonylmethyl. $\alpha$-Hydroxyalkyl $R_1$ has, in particular, 1–6 C atoms, such as hydroxymethyl or $\alpha$-hydroxyethyl, and is in particular esterified with alkylcarbonyl or arylcarbonyl, as indicated for $R_2$. $\alpha$-Hydroxycycloalkylmethyl $R_1$ has, in particular, 6–12 C atoms, such as hydroxy-(cyclohexyl)-methyl, and can be esterified as indicated above. $\alpha$-Hydroxyaralkyl $R_1$ has, in particular, 7–12 C atoms, such as $\alpha$-hydroxybenzyl, and can be esterified as indicated above. Cycloalkoxymethyl $R_1$ has, in particular, 6–12 C atoms, such as cyclohexyloxymethyl, and the same applies in the case of cycloalkylthiomethyl. Aralkoxymethyl or aralkylthiomethyl $R_1$ has, in particular, 8–13 C atoms, such as benzyloxymethyl. Alkoxy $R_1$ has, in particular, 1–6 C atoms, such as methoxy. Alkylthio $R_1$ has, in particular, 1–6 C atoms, such as methylthio. Alkoxymethyl and alkylthiomethyl $R_1$ have, in particular, 1–18 C atoms in the alkyl moiety, such as methoxymethyl, ethoxymethyl, methylthiomethyl or ethylthiomethyl. Aryloxymethyl and arylthiomethyl $R_1$ are, in particular, those radicals in which aryl is substituted or unsubstituted phenyl, such as phenoxymethyl or phenylthiomethyl. What has been stated with regard to $R_1$ applies equally in the case of $R_2$ and $R_3$ when these are the radicals defined for $R_1$. Halogen $R_1$, $R_2$ and $R_3$ are, for example, bromine, fluorine and in particular chlorine.

As carboxyl in the form of a salt, $R_2$ is, in particular, carboxyl which has been converted to a salt with one equivalent of calcium, barium, zinc, cadmium, antimony, diorgano-tin, such as dialkyl-tin, or in particular magnesium.

Acyl $R_2$ is in particular formyl, alkoxycarbonyl, arylcarbonyl or free, esterified or amidated carboxyl.

Alkylcarbonyl $R_2$ is, in particular, alkylcarbonyl having 2–19 C atoms, such as propionyl, butyryl, lauroyl or in particular acetyl. Arylcarbonyl $R_2$ is in particular arylcarbonyl having 7–19 C atoms, such as substituted or unsubstituted benzoyl and in particular benzoyl itself. Esterified carboxyl $R_2$ is in particular carboxyl esterified with a monohydric to tetrahydric aliphatic, cycloaliphatic or araliphatic alcohol having 1–20 C atoms, and preferably a dihydric alcohol is esterified with two pyrrolecarboxylic acid molecules, a trihydric alcohol is esterified with three pyrrolecarboxylic acid molecules and a tetrahydric alcohol is esterified with four pyrrolecarboxylic acid molecules. Suitable monohydric alcohols are, for example, $C_1-C_{18}$-alkanols, such as methanol, ethanol, n-octanol or lauryl alcohol, $C_5-C_{19}$-aralkanols, such as benzyl alcohol or furfuryl alcohol, or $C_5-C_8$-cycloalkanols, such as cyclohexanol. Suitable dihydric alcohols are, for example, $C_2-C_{20}$-alkanediols, such as ethylene glycol or 1,2-butylene glycol, $C_{4-20}$oxaalkanediols, such as 3-oxa-1,5-dihydroxypentane, or $C_{4-20}$-thiaalkanediols, such as 3-thia-1,5-dihydroxy-pentane. Suitable trihydric alcohols are, for example, $C_{3-20}$-alkanetriols, such as glycerol, or tris-$\beta$-hydroxyethyl isocyanurate, and suitable tetrahydric alcohols are, for example, $C_{4-20}$-alkanetetrols, such as pentaerythritol. ($C_{1-18}$-Alkoxy)-carbonyl $R_2$ is particularly preferred. Amidated carboxyl $R_2$ is, in particular, arylaminocarbonyl, in which aryl has in particular 6–18 C atoms, such as phenylaminocarbonyl, which can be substituted, for example by $C_{1-6}$ alkyl, $C_{1-6}$ alkoxy and/or hydroxyl, and in particular phenylaminocarbonyl itself or m-hydroxyphenylaminocarbonyl, or ($C_{1-18}$-alkyl)-aminocarbonyl, such as methylaminocarbonyl or ethylaminocarbonyl. Suitable alcohols in esterified carboxyl are, in particular, also those containing epoxy groups, such as monohydric alcohols of this type, for example a glycidyl ester or an epoxidised oleyl ester.

If $R_2$ together with $R_1$ is —CO-alkylene, alkylene has, in particular, 2–10 C atoms and 2 or 3 chain C atoms, such as ethylene, 1,3-propylene or 2,2-dimethyl-1,3-propylene.

As alkyl, aryl, alkoxymethyl, alkylthiomethyl, aryloxymethyl and arylthiomethyl, $R_3$ is, in particular, the radicals defined under $R_1$, $R_3$ and $R_1$ being independent of one another, and is in particular methyl or alkoxymethyl and especially phenyl.

Salts of pyrroles of the formula I are, in particular, N-metal salts, such as have been mentioned for carboxyl $R_2$ in the form of a salt, such as pyrroles which have been converted to a salt with one equivalent of calcium, barium, zinc, cadmium, antimony, diorgano-tin, such as dialkyl-tin, for example di-n-dibutyl-tin, or in particular magnesium.

Preferably, the chlorine-containing thermoplastics according to the invention contain those pyrroles of the formula I in which $R_1$ is phenyl, $R_2$ is hydrogen or methyl and $R_3$ is phenyl, and especially also those in which $R_1$ is methyl, $R_2$ is a carboxyl mono-esterified to tetraesterified with a monohydric to tetrahydric $C_{1-20}$ alcohol, or aminocarbonyl or arylaminocarbonyl and $R_3$ is aryl, and in particular those in which $R_1$ is methyl, $R_2$ is as defined above and $R_3$ is phenyl.

The pyrroles of the formula I which are used are in particular those in which $R_1$ is hydrogen, alkyl, cycloalkyl, aryl, alkoxycarbonylmethyl, hydroxymethyl, alkoxymethyl, alkylthiomethyl, aryloxymethyl or arylthiomethyl, $R_2$ is cyano, free carboxyl or carboxyl in the form of a salt, or acyl, it being possible for acyl together with $R_1$ to be -CO-alkylene, in which —CO— is bonded in the 3-position, and $R_3$ is alkyl, aryl, hydroxymethyl, alkoxymethyl, alkylthiomethyl, aryloxymethyl or arylthiomethyl.

Pyrroles of the formula I which are particularly preferentially used are those in which $R_1$ is methyl or phenyl, $R_2$ is cyano, $C_{2-19}$-alkylcarbonyl, $C_{7-19}$-arylcarbonyl or carboxyl which is esterified with a $C_{1-18}$-alkanol, $C_{5-8}$-cycloalkanol, $C_{5-19}$-aralkanol, $C_{2-20}$-alkanediol or $C_{4-20}$-thiaalkanediol or with pentaerythritol, and $R_3$ is methyl, phenyl or ($C_{1-18}$-alkoxy)-methyl.

Preferably, the pyrroles of the formula I which are used are those in which $R_1$ is methyl, $R_2$ is $C_{2-19}$-alkylcarbonyl or in particular carboxyl which is esterified with a $C_{1-18}$-alkanol, $C_{2-20}$-alkanediol or $C_{4-20}$-thiaalkanediol or with pentaerythritol, and $R_3$ is phenyl, and in particular the pyrroles mentioned in the examples, and amongst the latter especially:

(a) 2-methyl-3-cyclohexyloxycarbonyl-4-phenyl-pyrrole,
(b) 2-methyl-3-benzyloxycarbonyl-4-phenyl-pyrrole,
(c) 2-phenyl-3-ethoxycarbonyl-4-methyl-pyrrole,
(d) 2-methyl-3-benzoyl-4-phenyl-pyrrole,
(e) 2-methyl-3-ethoxycarbonyl-4-phenyl-pyrrole,
(f) 2,4-diphenyl-pyrrole,
(g) 2-methyl-3-phenylaminocarbonyl-4-phenyl-pyrrole,
(h) 2-methyl-3-meta-hydroxyphenylaminocarbonyl-4-phenylpyrrole and
(i) 2,4-diphenyl-3-($\alpha$-hydroxy-ethyl)-pyrrole.

Pyrroles are compounds which have been known for a long time. Thus, in Ber. 35, 3,004 (1902) Knorr and Lange describe the preparation of pyrroles by reaction of aminoketones, such as aminoacetophenone or aminoacetone, with an acylacetone, such as ethyl acetoacetate or acetylacetone. Thus, 2,4-dimethyl-3-ethoxycarbonylpyrrole is obtained from aminoacetone and ethyl acetoacetate, and 2,4-dimethyl-3-acetyl-pyrrole is obtained from aminoacetone and acetylacetone. The reaction is advantageously carried out in the presence of a buffer, such as sodium acetate/acetic acid. According to Benary, Ber. 44, 405 (1911) it is also possible in the above reaction to replace the aminoketone by a chloroaldehyde and ammonia, such as by chloroacetaldehyde and ammonia, for example in the form of a 10% ammonia solution. In the case of chloroacetaldehyde, 2,3-substituted pyrroles are obtained, for example 2-methyl-3-ethoxycarbonylpyrrole is obtained from chloroacetaldehyde, ammonia and ethyl acetoacetate. A summary of pyrrole chemistry is published in the monograph by R. A. Jones, "The Chemistry of Pyrroles", Academic Press 1977.

The pyrroles are incorporated in the chlorinecontaining thermoplastics to be stabilised before the latter are processed in conventional devices and in general are incorporated in amounts of 0.05 to 5 and preferably of 0.1 to 3% by weight, based on the chlorinecontaining thermoplastics.

In addition, it is also possible to use conventional PVC stabilisers in the customary amounts, such as organo-tin stabilisers, epoxy compounds, preferably epoxidised fatty acid esters, such as epoxidised soya bean oil, phosphites, especially mixed aryl/alkyl phosphites, phenolic antioxidants, metal carboxylate stabilisers, such as calcium carboxylates, especially calcium stearates, and also carboxylates of cadmium, zinc and barium. Costabilisers are preferably incorporated in amounts of 0.05 to 5 and especially 0.1 to 3% by weight. The ratio of pyrrole to costabilisers can be about 2:1 to 1:8. Suitable metal stabilisers are the carboxylates or phenolates of the metals barium, calcium, zinc or cadmium. The phenols can have 6 to 20 C atoms and the carboxylic acids can preferably have 8 to 20 C atoms. Mixtures of barium salts and cadmium salts or calcium salts and zinc salts are particularly advantageous.

Vinyl chloride polymers or copolymers are preferably used for the moulding compositions according to the invention. Preferred polymers are suspension polymers and mass polymers and washed emulsion polymers, i.e. emulsion polymers with a low emulsifier content. Suitable comonomers for the copolymers are, for example: vinyl acetate, vinylidene chloride, transdichloroethylene, ethylene, propylene, butylene, maleic acid, acrylic acid, fumaric acid and itaconic acid. Further suitable chlorine-containing polymers are post-chlorinated PVC and chlorinated polyolefins, and also graft polymers of PVC with EVA and MBS.

The stabilised thermoplastics according to the invention are prepared by known processes, by incorporating the stabilisers and, if desired, further stabilisers into the polymer. A homogeneous mixture of stabiliser and PVC can be obtained, for example, with the aid of a two-roll mixer at 150°–210° C.

Depending on the intended use of the moulded composition, it is also possible to incorporate further additives before or at the same time as incorporating the stabiliser; such additives are, for example, lubricants (preferably montan waxes or glycerol esters), fatty acid esters, paraffins, plasticisers, fillers, modifiers (such as additives which impart high impact strength), pigments, light stabilisers, UV absorbers, antioxidants or further costabilisers, for example phosphites. The thermoplastics according to the invention can be processed to mouldings by the shaping process customary for this purpose, for example by extrusion, injection moulding or calendering. Use as plastisols is also possible.

The heat stabilisation with the stabilisers used according to the invention is outstanding in the thermoplastics according to the invention. The stability to light is also good.

The examples which follow serve to illustrate the invention in more detail. Parts and percentages are by weight.

EXAMPLES 1–7

General synthesis example: A mixture of 0.1 mol of α-aminoketone hydrochloride*, 0.12 mol of sodium acetate and 0.1 mol of ethyl acetoacetate or 1,3-diketone in 100 g of 75% acetic acid is heated on a waterbath for 1 hour, with stirring. After cooling, the reaction mixture is stirred into cold water and the reaction product which has precipitated is filtered off with suction and recrystallised.
*in place of the aminoketone hydrochloride it is also possible to use an α-nitrosoketone, which under the reaction conditions—if a suitable reducing agent is used—is reduced to the α-aminoketone and simultaneously reacted.

In the case of reaction products which are obtained as oily or liquid products, the aqueous solution is extracted with toluene or chloroform, the toluene solution is dried over sodium sulfate and filtered, the filtrate is concentrated by means of a rotary evaporator and the residue is distilled (high vacuum) or recrystallised.

In addition to known pyrrole derivatives, the following pyrrole derivatives which have not previously been described have also been synthesised by this process.
2-Methyl-3-carboxymethyl-4-phenylpyrrole (Example 1, stabiliser No. 10), melting point 132°–133° C.; structure established by $^{13}$C-NMR spectroscopy.
2-Methyl-3-carboxylauryl-4-phenylpyrrole (Example 2, stabiliser No. 5), melting point 51°–52° C.; structure established by $^{13}$C-NMR spectroscopy.
Thiodiethylene glycol bis-(2-methyl-4-phenylpyrrole-3-carboxylate) (Example 3, stabiliser No. 9), melting point 161°–163° C.; structure established by $^{13}$C-NMR spectroscopy. 2,4-Diphenyl-3-(α-hydroxyethyl)-pyrrole, melting point 128° C. (Example 4, stabiliser No. 15).
2-Methyl-3-phenylaminocarbonyl-4-phenyl-pyrrole (Example 5, stabiliser No. 14).
2-Methyl-3-meta-hydroxyphenylaminocarbonyl-4-phenylpyrrole (Example 6).
2-Methyl-3-cyclohexyl-oxycarbonyl-4-phenyl-pyrrole (Example 7, stabiliser No. 12).

EXAMPLE 8

Test data based on DIN 53,381, sheet 3 (dehydrochlorination test) for stabilisers according to the invention
Concentration: concentration based on PVC (S-PVC, K value 64)
Induction time: time which elapses before the dehydrochlorination curve starts to rise
Elimination time: time which elapses before 0.5% of the available chlorine has been eliminated
Tangent: gradient of the curve at "elimination time 0.5%".

| Stabiliser No. | Stabiliser(s) | Concentration [%] | Induction time [min.] | Elimination time [min.] | Tangent |
|---|---|---|---|---|---|
| Comparison | None | — | 12 | 40 | 0.93 |
| 1 | H₃C, CO—CH₃ / CH₃ / N-H (pyrrole) | 0.34* | 23 | 68 | 0.55 |
| 2 | H₃C, CO—O—Et / CH₃ / N-H (pyrrole) | 0.42* | 16 | 50 | 0.74 |
| 3 | Ph, CO—CH₃ / CH₃ / N-H (pyrrole) | 0.50* | 20 | 83 | 0.41 |
| 4 | Ph, CO—O—Et / CH₃ / N-H (pyrrole) | 0.57* | 20 | 100 | 0.33 |

-continued

| Stabiliser No. | Stabiliser(s) | | Concentration [%] | Induction time [min.] | Elimination time [min.] | Tangent |
|---|---|---|---|---|---|---|
| Comparison | Epoxidised soya bean oil = ESO | | 1.0 | 19 | 52 | 0.76 |
| 4 | Ph, CO—O—Et / CH₃ pyrrole (NH) | ESO +  | 1.0 0.58 | 35 | 119 | 0.31 |
| 5 | Ph, CO—O—Lau / CH₃ pyrrole (NH) | ESO + | 1.0 0.94 | 32 | 115 | 0.31 |
| 6 | H₃C, CO—O—Et / Ph pyrrole (NH) | ESO + | 1.0 0.58 | 32 | 91 | 0.38 |
| 7 | Ph, CO—CH₃ / —CH₂—CO—O—CH₃ pyrrole (NH) | ESO + | 1.0 0.68 | 23 | 88 | 0.40 |
| 8 | Ph, CO—Ph / CH₃ pyrrole (NH) | ESO + | 1.0 0.65 | 30 | 98 | 0.38 |
| 9 | Ph, (CO—O—CH₂—CH₂—)₂S / CH₃ pyrrole (NH) | ESO + | 1.0 0.61 | 32 | 110 | 0.28 |
| 10 | Ph, CO—O—CH₃ / CH₃ pyrrole (NH) | ESO + | 1.0 0.54 | 35 | 125 | 0.30 |
| 11 | Ph, CO—O—Et / Ph pyrrole (NH) | ESO + | 1.0 0.73 | 42 | 130 | 0.25 |
| Comparison | Epoxidised soya bean oil = ESO | | 2.0 | 26 | 64 | 0.67 |
| 4 | Ph, CO—O—Et / CH₃ pyrrole (NH) | ESO + | 2.0 1.0 | 40 | 152 | 0.23 |
| 4 | Ph, CO—O—Et / CH₃ pyrrole (NH) Ph—O—P(—O—C₁₀H₂₁)₂ | ESO + | 2.0 0.75 0.75 | 55 | 142 | 0.30 |
| Comparison | Epoxidised soya bean oil Ca stearate Zn stearate | | 3.0 0.2 0.2 | 29 | 45 | 1.63 |
| 1 | Epoxidised soya bean oil Ca stearate Zn stearate Ph, CO—CH₃ / CH₃ pyrrole (NH) | + | 3.0 0.2 0.2 0.4 | 47 | 65 | 1.44 |
| 4 | Epoxidised soya | | | | | |

-continued

| Stabiliser No. | Stabiliser(s) | Concentration [%] | Induction time [min.] | Elimination time [min.] | Tangent |
|---|---|---|---|---|---|
| | bean oil | 3.0 | | | |
| | Ca stearate | 0.2 | | | |
| | Zn stearate | 0.2 | 49 | 75 | 1.0 |
| | Ph–[pyrrole(CO—O—Et, CH₃)]–NH | + 0.4 | | | |
| 4 | Ph–[pyrrole(CO—O—Et, CH₃)]–NH | ESO 0.5 + 0.5 | 29 | 107 | 0.33 |
| | | ESO 1.0 + 1.0 | 35 | 125 | 0.29 |
| | | ESO 1.5 + 1.5 | 40 | 140 | 0.26 |

*corresponding to 2.5 mmols per 100 g of PVC

EXAMPLE 9

Test results for compounds according to the invention in the static heating test at 180° C. S-PVC+2% of epoxidised soya bean oil+2.5 mmol% of stabiliser.

| Stabiliser No. | Stabilisers | Yellowness indices | | |
|---|---|---|---|---|
| | | Mill hide | 10 mins. | 20 mins. |
| 12 | Ph–[pyrrole(CO—O—C$_y$, CH₃)]–NH | 5.4 | 16.7 | 28.7 |
| 13 | Ph–[pyrrole(CO—N(Et)₂, CH₃)]–NH | 8.1 | 21.5 | 38 |
| 14 | Ph–[pyrrole(CO—N(H)—Ph, CH₃)]–NH | 5.4 | 18.2 | 34 |
| 15 | Ph–[pyrrole(—, Ph)]–NH | 4.4 | 12.0 | 21.3 |

What is claimed is:

1. A chlorine-containing thermoplastic, containing a pyrrole of the formula I

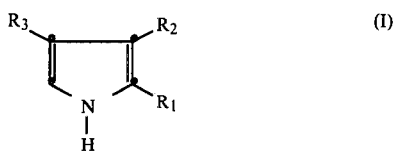

in which $R_1$ is hydrogen, alkyl, cycloalkyl, aryl, alkoxycarbonylmethyl, free or esterified α-hydroxyalkyl, free or esterified α-hydroxycycloalkylmethyl, free or esterified α-hydroxyaralkyl, alkoxymethyl, alkylthiomethyl, aryloxymethyl, arylthiomethyl, cycloalkoxymethyl, cycloalkylthiomethyl, aralkoxymethyl, aralkylthiomethyl, alkoxy, alkylthio, cycloalkoxy, cycloalkylthio, aralkoxy, arylalkylthio, aryloxy, arylthio, halogen, mercapto, mercaptomethyl or hydroxyl, $R_2$ is hydrogen, alkyl, cycloalkyl, aryl, free or esterified α-hydroxyalkyl, in which the alkyl moiety together with $R_1$ can be alkylene, or free or esterified α-hydroxycycloalkylmethyl, free or esterified α-hydroxyaralkyl, alkoxy, cycloalkoxy, aralkoxy, aryloxy, alkylthio, cycloalkylthio, aralkylthio, arylthio, alkoxymethyl, alkylthiomethyl, aryloxymethyl, arylthiomethyl, cycloalkoxymethyl, cycloalkylthiomethyl, aralkoxymethyl, aralkylthiomethyl, hydroxyl, cyano, free carboxyl or carboxyl in the form of a salt or an ester, or acyl, it being possible for acyl together with $R_1$ to be —CO-alkylene, in which —CO— is bonded in the 3-position, or $R_2$ is halogen, mercapto or mercaptomethyl, and $R_3$ is alkyl, cycloalkyl, aralkyl, aryl, free or esterified hydroxymethyl, alkoxymethyl, alkylthiomethyl, cycloalkoxymethyl, cycloalkylthiomethyl, aralkoxymethyl, arylalkylthiomethyl, aryloxymethyl or arylthiomethyl, alkoxy, alkylthio, cycloalkoxy, cycloalkylthio, aralkoxy, aralkylthio, aryloxy, arylthio, halogen, mercapto or mercaptomethyl, or if $R_2$ is carboxyl in the form of a salt, $R_3$ is hydrogen and $R_1$ is as defined, or in which $R_3$ is hydroxyl and $R_1$ is hydrogen, alkyl or aryl and $R_2$ is hydrogen, alkyl, aryl or acyl, or a salt thereof.

2. A chlorine-containing thermoplastic according to claim 1, wherein $R_1$ is aryl, $R_2$ is hydrogen or $C_{1-6}$-alkyl and $R_3$ is aryl.

3. A chlorine-containing thermoplastic according to claim 1, wherein $R_1$ is phenyl, $R_2$ is hydrogen or methyl and $R_3$ is phenyl.

4. A chlorine-containing thermoplastic according to claim 1, wherein $R_1$ is methyl, $R_2$ is a carboxyl which is mono-esterified to tetra-esterified with a monohydric to tetrahydric $C_{1-20}$-alcohol, or aminocarbonyl or arylaminocarbonyl, and $R_3$ is aryl.

5. A chlorine-containing thermoplastic according to claim 1, wherein $R_1$ is methyl, $R_2$ is as defined in claim 4 and $R_3$ is phenyl.

6. A chlorine-containing thermoplastic according to claim 1, wherein $R_1$ is hydrogen, alkyl, cycloalkyl, aryl, alkoxycarbonylmethyl, hydroxymethyl, alkoxymethyl, alkylthiomethyl, aryloxymethyl or arylthiomethyl, $R_2$ is cyano, free carboxyl or carboxyl in the form of a salt or an ester, or acyl, it being possible for acyl together with $R_1$ to be —CO— alkylene, in which —CO— is bonded in the 3-position, and $R_3$ is alkyl, aryl, hydroxymethyl, alkoxymethyl, alkylthiomethyl, aryloxymethyl or arylthiomethyl.

7. A chlorine-containing thermoplastic according to claim 6, wherein $R_1$ is methyl or phenyl, $R_2$ is cyano, $C_{2-19}$-alkylcarbonyl, $C_{7-19}$-arylcarbonyl or carboxyl which is esterified with a $C_{1-18}$-alkanol, $C_{5-8}$-cycloalkanol, $C_{5-19}$-aralkanol, $C_{2-20}$-alkanediol or $C_{4-20}$-thiaalkanediol or with pentaerythritol, and $R_3$ is methyl, phenyl or ($C_{1-18}$-alkoxy)-methyl.

8. A chlorine-containing thermoplastic according to claim 1, containing 2,4-diphenyl-pyrrole.

9. A chlorine-containing thermoplastic according to claim 1, containing 2-methyl-3-cyclohexyloxycarbonyl-4-phenyl-pyrrole, 2-methyl-3-benzyloxycarbonyl-4-phenylpyrrole, 2-phenyl-3-ethoxycarbonyl-4-methyl-pyrrole, 2-methyl-3-benzoyl-4-phenyl-pyrrole, or 2-methyl-3-ethoxycarbonyl-4-phenyl-pyrrole, 2-methyl-3-phenylaminocarbonyl-4-phenyl-pyrrole, 2-methyl-3-meta-hydroxyphenylaminocarbonyl-4-phenyl-pyrrole or 2,4-diphenyl-3-($\alpha$-hydroxyethyl)-pyrrole.

10. A chlorine-containing thermoplastic according to any one of claims 1 to 9, containing a pyrrole of the formula I in an amount of 0.05 to 5% by weight.

11. A chlorine-containing thermoplastic according to any one of claims 1 to 10, additionally containing one or more conventional PVC stabilisers and/or additives.

12. A chlorine-containing thermoplastic according to any one of claims 1 to 11, wherein the substrate is PVC.

13. A method for stabilizing a chlorine-containing thermoplastic which comprises incorporating therein an effective amount of a pyrrole according to any one of claims 1 to 9.

* * * * *